| United States Patent [19] | [11] Patent Number: 4,879,116 |
| Fox et al. | [45] Date of Patent: Nov. 7, 1989 |

[54] SKIN PROTEIN COMPLEXING COMPOSITION FOR THE POTENTIATION OF THE SUBSTANTIVITY OF ALUMINUM ACETATE THROUGH THE USE OF A CATIONIC EMULSIFIER AS AN AID IN SKIN HEALING

[76] Inventors: Charles Fox, 39-08 Tierney Pl., Fairlawn, N.J. 07410; John W. DeWitt, 9 Parker Ct., Florham Park, N.J. 07932; John D. Rothenberger, Jr., 303 Parkside Rd., Harrington Park, N.J. 07640

[21] Appl. No.: 207,871

[22] Filed: Jun. 13, 1988

[51] Int. Cl.$^4$ .............................................. A01N 59/06
[52] U.S. Cl. .................................... 424/682; 514/827; 514/847; 514/848
[58] Field of Search .................. 424/154, 20; 514/847, 514/848, 938, 827

[56] References Cited

U.S. PATENT DOCUMENTS

| 4,719,099 | 1/1988 | Grollier et al. | 424/78 |
| 4,725,433 | 2/1988 | Matravers | 424/70 |
| 4,737,361 | 4/1988 | Rafft et al. | 424/47 |

*Primary Examiner*—Thurman K. Page
*Assistant Examiner*—P. L. Prater
*Attorney, Agent, or Firm*—Darby & Darby

[57] ABSTRACT

A skin protein precipitation potentiating lotion or cream utilizing aluminum acetate and the cationic surfactant salts of strong acids to promote the healing of damaged skin cells.

6 Claims, No Drawings

SKIN PROTEIN COMPLEXING COMPOSITION FOR THE POTENTIATION OF THE SUBSTANTIVITY OF ALUMINUM ACETATE THROUGH THE USE OF A CATIONIC EMULSIFIER AS AN AID IN SKIN HEALING

SUMMARY OF THE INVENTION

It is the main object of this invention to potentiate and prolong the skin healing and moisturizing actions of aluminum compounds by enhancing their substantivity to the skin by combining them in emulsions or solutions containing the chloride, bromide, or sulfate salts of cationic surface active agents.

It is also the objective of this invention to provide a more effective skin healing product by utilizing cationic surfactant salts of strong acids to stabilize the aluminum acetate and to enhance its activity.

This combination has been found useful for the purpose of restoring the integrity of damaged individual skin cells and capillaries, enabling them to retain the body's natural healing fluids and promote and accelerate the healing of the skin.

It is known that aluminum acetate precipitates the skin's own protein material on damaged skin areas. Cationic surface active agents are also known to bind to the skin. But it has been surprisingly learned that the combination of aluminum acetate with the chloride, bromide, or sulfate salts of cationic surfactants produce a synergistic substantive effect which is unexpected and novel.

A result of this combination has been found to be long-lasting cell and capillary healing and skin moisturizing actions which are unique to the art.

The invention described in this patent discloses a new skin healing and moisturizing composition in the form of an oil-in-water emulsion lotion or cream comprising:

1. From about 0.1% to about 5.0% of a topical astringent-preferably aluminum acetate.
2. An oil-in-water emulsion in the form of a lotion or cream, said emulsion utilizing a cationic or combination of cationic/nonionic emulsifying agents. The concentration of said emulsifying agent or agents is from about 0.25% to 10.0%.
3. From about 0.1% to 3.0% of a cationic surfactant-preferably Steapyrium Chloride.
4. An oil-in-water emulsion in lotion or cream form containing an oil phase composed of one or more oils taken from the class of triglycerides, fatty acid esters, lanolin, or lanolin derivatives, hydrocarbons including mineral oil, petrolatum, paraffin, as well as silicones including dimethicone and cyclomethicone. The oil phase comprises from about 3.0% to 50% of the composition.
5. An oil-in-water emulsion in cream or lotion form containing a humectant such as propylene glycol, glycerin, or sorbitol or a combination of these humectants in a concentration from about 3.0% to about 30.0%.

DETAILED DESCRIPTION OF THE INVENTION

Human skin consists of two major parts. The uppermost, thinner part is called the epidermis. The epidermis is divided into two major parts: the surface stratum corneum, consisting of about 20 or more compact layers of dead skin cells, and a basal layer, several underlying layers of viable, living cells, and the dermis which underlies the epidermis.

The stratum corneum serves as the protective layer or barrier which prevents environmental poisons and irritants from entering the body, protects against damage from physical abrasion, and also regulates the loss of moisture from the body.

The outermost layer of cells of the stratum corneum are subject to wear and tear, being worn away and sloughed off by rubbing actions.

The primary function of the basal layer of the epidermis is to provide cells which move upward into the epidermis, where they become keratinized (i.e. form keratin fibrils) and eventually die and become part of the stratum corneum barrier layer. Thus, as the stratum corneum loses its outermost cells, new cells are continually added to it. This entire process can take from about three to four weeks.

The dermis underlying the epidermis contains capillaries and blood vessels which supply nourishment for the living epidermal cells and also contains cells which manufacture collagen and elastin fibers and mucopolysaccharides all of which provide turgor, elasticity, and structural strength. A detailed description of the structure and function of the skin may be found in "The Structure and Function of Skin," 3rd Edition, W. Montagne and P. F. Parrakal, Academic Press, N.y. 1974, and "The Dermis," edited by W. Montagna, J. P. Bentley, and R. L. Dobson, Appleton-Century-Crofts, Meredith, N.Y., 1970.

The stratum corneum is primarily proteinaceous in nature and should contain at least 10% of water to remain soft, pliable and plasticized. It has been shown that if the moisture content falls below this level the skin becomes dry and rough. This phenomenon was first recognized by Dr. I. H. Blank and described in articles published in The Journal of Investigative Dermatology, Vol. 18, pps. 433–440 (1952) and Vol. 21 of the same journal, pages 259–271 (1953).

The stratum corneum contains materials that have the ability to hold some moisture and these include, in part, amino acids, lactic acid and its salts, urea, sugars, and condensation products of sugars with amino acids. This group of materials has been referred to in the past as the skin's natural moisturizing factor, or NMF. Under conditions of low relative humidity, such as exist in heated homes during the cold winter months, or when the skin is exposed to cold weather or wind, the skin's natural NMF does not retain sufficient moisture in the stratum corneum which becomes dry, rough, and brittle. It has also been shown that frequent exposure of the skin to alkaline soaps, to dishwashing and laundering detergents, and to solvents depletes the skin of its natural NMF components and this also reduces the quantity of water that the stratum corneum can hold.

When the skin is in this dry condition, it becomes chapped and develops cracks and fissures. The skin, then, has lost the continuity of its protective barrier and environmental pollutants and irritants can then enter into the living portion of the skin resulting in irritation, erythema, inflammation, and pruritis.

The resulting irritation and inflammation is due to the exposure of the living cells and the capillary bed in the skin. Exudation (oozing) of body fluids from cells and capillaries occurs. The healing process occurs through tissue regrowth on the affected area.

Many preparations such as hand lotions and creams and moisturizing lotions and creams are sold for the treatment of dry, irritated, inflamed, and damaged skin. These preparations are mainly oil-in-water emulsions and deposit a layer of oil on the skin to retard the moisture loss and thus build up a higher concentration of moisture in the stratum corneum. Many preparations also contain humectants such as glycerin, propylene glycol, and sorbitol to further aid in retaining moisture in the stratum corneum. The great majority of these preparations contain from 2% to 5% of soaps such as triethanolamine stearate, potassium stearate, or sodium stearate as emulsifying agents. They are also formulated with from 75% to 85% of water. When the water evaporates after application, a layer of solids remains on the skin which may contain from 10% to 20% of soap. Rather than alleviating the dry, irritated skin condition, these alkaline soaps left on the skin further aggravate the conditions since, as mentioned above, soaps further dissolve away the natural moisturizers reducing the quantity of moisture held by the stratum corneum, inhibit the coagulation of body fluids needed for healing exuding from exposed cells and capillaries, and, because soaps are alkaline in nature, act as further irritants thus aggravating the redness and inflammation.

None of the leading preparations being marketed today for the treatment of dry irritated skin contain pharmacological agents that will both help heal the skin and increase the moisture retention in the skin.

Therefore, it is the object of this invention to optimize the protein precipitation potential of astringents to promote healing by precipitating protein to stop the leaking of cellular growth promoters in fluids exuded by damaged skin cells and capillaries and increase the moisture retention of the skin by potentiating the substantivity of a skin lotion and cream to the skin.

Astringents are useful to provide mechanical or physical protection to the skin which, in turn, may prevent further skin irritation. The skin is often subjected to injuries and astringents, applied locally, are protein precipitants which have such a low cell permeability that the action is essentially limited to the cell surface and to the interstitial spaces. The permeability of the cell membrane is reduced but the cells remain viable. The astringent action is accompanied by a contraction of the tissue and by blanching of the affected area. The cement substance of the capillary endothelium is hardened and thus the transcapillary movement of plasma is inhibited and local edema, inflammation, and exudation are thereby reduced. This is more fully discussed in the chapter on "Topical Drugs" by S. C. Harvey in Remington's Pharmaceutical Sciences, 15th edition, edited by J. Hoover, Mack Publishing Co., Easton, Pa., pages 716–717, 1975.

Thus, astringents are employed therapeutically to reduce inflammation, to promote healing, and to toughen the skin. Acceptable astringents are those listed in The Federal Register, Vol. 47, No. 173, of Sept. 7, 1982, in the Food and Drug Administrations's monograph on Skin Protectant Drug Products for Over-The-Counter Human Use.

These include aluminum acetate (Burows' Solution), aluminum sulfate, and witch hazel. Our preferred astringent is aluminum acetate but other astringents such as the salts of zinc, manganese, iron, and bismuth, tannins or related polyphenolic compounds and certain acids, alcohols and phenols that precipitate proteins, will also operate effectively in the invention. Our preferred product contains from about 0.1% to about 5.0% of aluminum acetate.

The oil-in-water emulsion used as the vehicle for the product described in this invention preferably utilizes a cationic surfactant as the emulsifying agent. This type of emulsion is preferred because it provides an emulsion with a pH value which is similar to that of the skin. The cationic surfactants are also substantive to the skin keratin proteins and after application, become bound to the skin proteins forming a water insoluble complex. The cationic surfactant thus loses its surface activity and the resultant insoluble complex enhances the natural barrier action of the stratum corneum, aids in retarding moisture loss, thus increases the moisture content of the stratum corneum, and which protects the skin against further wash-out of its natural water-holding and tissue growth promoting materials.

Suitable cationic emulsifying agents include N-(Stearoyl Colamino Formyl Methyl) Pyridinium Chloride, and N-(Lauroyl Colamino Formyl Methyl) Pyridinium Chloride which are marketed as Emcol E-6075 and Emcol E-607, respectively, by Witco Chemical Corporation. Stearamidoethyl diethylamine phosphate, cetyl trimethylammonium bromide, stearyl dimethyl benzyl ammonium chloride, and distearyldimethyl ammonium chloride can also be used as the cationic emulsifying agents. There are many more cationic emulsifying agents available and known to those familiar with the art of formulating emulsions and therefore it should not be construed that the cationic emulsifying surfactants mentioned above are the only cationic emulsifying agents that will be effective in the product described in this invention.

Aluminum acetate as mentioned above is an approved category I skin astringent under the Skin Protectant Monograph. Unfortunately in the presence of water, aluminum acetate loses some of its potency because of the formation of aluminum hydroxide which is insoluble and does not have the healing or astringent properties of aluminum acetate. The hydrolysis occurring is shown in equation I below.

Equation 1:

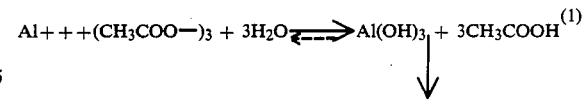

We have now found that the incorporation of aluminum acetate in cosmetic emulsions of solutions containing the chloride, bromide, or sulfate salts of cationic surface active agents considerably enhance the activity and efficacy of aluminum acetate. First, the cationic surfactant is substantive to the proteins in the skin. When the occurs, a hydrogen ion is released and this combines with the anion previously introduced by the cationic surfactant to form a small quantity of the corresponding such as hydrochloric, hydrobromic or sulfuric acid. This reaction is illustrated generically in equation (2).

Equation 2:

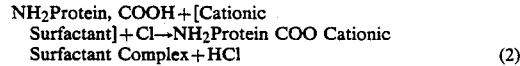

The hydrochloric acid so released prevents the precipitation of aluminum hydroxide by reacting with it and forming aluminum chloride, as shown in equation (3). The release of hydrochloric (or sulfuric) acid lowers the pH, prevents the formation of aluminum hydroxide and thus actually improves the action of the aluminum acetate by forming a small portion of aluminum chloride which is a more potent astringent.

Equation 3:

$$Al(OH)_3 + 3HCl \rightarrow AlCl_3 = 3H_2O \qquad (3)$$

Another unexpected advantage on the skin is that the cationic surfactant which contains a long chain aliphatic group imparts a velvety and cosmetically elegant feel to the skin which is not washed off with water.

A third and unexpected finding is that the combination of the aluminum acetate and cationic surfactant reduces the transepidermal moisture loss from the skin which results in superior skin moisturization and quicker healing of damaged skin. Some of the cationic surfactants (but not necessarily limted to these) which are operative include:

Distearyl Dimethyl Ammonium Chloride
Stearyl Benzyl Dimethyl Ammonium CChloride
Steapyrium Chloride
Stearamidoethyl Diethylamine Hydrochloride
Lapyrium Chloride
Cetyl Trimethyl Ammonium Chloride
Soyaethyl Morpholinium Ethosulfate An example of a formulation containing these materials is shown in Example No. 1.

EXAMPLE NO. 1

| Ingredient | Percent by Weight |
| --- | --- |
| Steapyrium Chloride | 1.00 |
| Aluminum Acetate | 1.00 |
| Jojoba Oil | 10.00 |
| Lanolin Oil | 2.00 |
| Petrolatum | 5.00 |
| Glycerin | 10.00 |
| Dimethicone | 1.00 |
| Fragrance and Preservative | qs |
| Deionized Water  qs | 100.00 |

SUMMARY OF THE INVENTION

The invention described in the patent discloses a synergistic and stabilized skin healing and soothing composition in the form of an oil-in-water emulsion lotion or cream comprising:

(a) From 0.1% to 5.0% of a topical astringent-preferably aluminum acetate.
(b) From 0.25% to 5.0% of a cationic surfactant salt where the accompanying anion is a chloride, bromide, or sulfate ion.
(c) An oil-in-water emulsion in the form of a lotion or cream utilizing from 0.24% to 5.0% of a cationic surfactant or from 0.25% to 10.0% of a combination of cationic/nonionic surfactants.

We claim:

1. A stabilized and synergistic therapeutic skin healing and soothing preparation for topical application to the skin containing from 0.1% to 5.0% of a topical astringent the Markush, "selected from the group consisting of aluminum acetate
   aluminum sulfate, witch hazel, salts of zinc maganese, iron and bismuth, tannins, polyphenolic compounds, acids alcohols and phenols capable of precipitating proteins, and from 0.25% to 5.0% of a cationic surfactant salt where the accompanying anion is a chloride, bromide, or sulfate ion.

2. A stabilized and synergistic therapeutic skin healing and soothing preparation for topical application to the skin containing from 0.1% to 5.0% of a topical astringent the Markush, "selected from the group consisting of aluminum acetate
   aluminum sulfate, witch hazel, salts of zinc maganese, iron and bismuth, tannins, polyphenolic compounds, acids alcohols and phenols capable of precipitating proteins, and from 0.25% to 5.0% of a cationic surfactant salt where the accompanying anion is a chloride, bromide, or sulfate ion or from 0.25% to 10.0% of a combination of such cationic surfactant and nonionic surfactant in an oil-in-water emulsion vehicle.

3. A composition as claimed in claim 1 where the topical astringent is aluminum acetate.

4. A composition as claimed in claim 1 where the cationic surfactant is steapyrium chloride.

5. A composition as claimed in claim 1 where the cationic surfactant is distearyl dimethyl ammonium chloride.

6. A composition as claimed in claim 2 where the cationic surfactant is steapyrium chloride and the nonionic surfactant is glyceryl monostearate.

* * * * *